United States Patent [19]

Hollstein et al.

[11] Patent Number: 4,918,041

[45] Date of Patent: Apr. 17, 1990

[54] CATALYST FOR HYDROCARBON CONVERSION AND CONVERSION PROCESS UTILIZING THE SAME

[75] Inventors: Elmer J. Hollstein, Wilmington, Del.; James T. Wei, Ridgewood, N.J.; Chao-Yang Hsu, Media, Pa.

[73] Assignee: Sun Refining and Marketing Company, Philadelphia, Pa.

[21] Appl. No.: 247,225

[22] Filed: Sep. 21, 1988

[51] Int. Cl.$^4$ .............................................. B01J 27/02
[52] U.S. Cl. ...................................................... 502/217
[58] Field of Search ................ 502/324, 217; 585/743, 585/750

[56] References Cited

U.S. PATENT DOCUMENTS

| | | | |
|---|---|---|---|
| 1,211,394 | 1/1917 | Bosch et al. | 502/324 |
| 2,399,927 | 5/1946 | Howes et al. | 585/750 |
| 3,032,599 | 5/1962 | Holm et al. | 585/750 |
| 3,132,110 | 5/1964 | Hansford et al. | 585/750 |
| 3,637,820 | 1/1972 | Dodman et al. | 502/324 |
| 3,743,683 | 7/1973 | Croce et al. | 502/324 |
| 3,903,242 | 9/1975 | Meissner et al. | 502/324 |
| 4,197,188 | 4/1980 | Antos | 585/743 |

*Primary Examiner*—Carl F. Dees
*Attorney, Agent, or Firm*—J. Edward Hess; Donald R. Johnson

[57] ABSTRACT

A sulfated calcined solid catalyst is provided which comprises (1) oxide or hydroxide or Group III or Group IV, e.g. zirconium, metal, (2) oxide or hydroxide or Group V, Group VI or Group VII, e.g. manganese, metal and (3) oxide or hydroxide or Group VIII, e.g. iron, metal. In one embodiment of the invention, the catalyst is used to isomerize normal alkanes having 4 to 7 carbon atoms per molecule, to obtain high octane number blending components for motor fuel and/or valuable chemical intermediates.

13 Claims, No Drawings

CATALYST FOR HYDROCARBON CONVERSION AND CONVERSION PROCESS UTILIZING THE SAME

This invention relates to novel catalysts suitable for various hydrocarbon conversions including isomerization of $C_4$ to $C_7$ acyclic hydrocarbons, alkylation of alkanes and alkylation of aromatics, dehydrogenation or partial oxidation of hydrocarbons and the conversion of alkenes and alcohols to ethers such as methyl tertiary butyl ether.

The invention also relates to novel catalytic isomerization processes employing the catalysts of the invention. Current commercial operations for n-butane isomerization include aluminum chloride and noble metal catalyzed processes. The aluminum chloride process, operated at relatively low temperature, is subject to corrosion and spent catalyst disposal problems. The high temperature noble metal process is subject to poisoning by sulfur and thus, added cost of feedstock pretreatment. Also, thermodynamic equilibrium limits the yield of isobutane from butane, and the need for a large butane separation tower for the product adds to the plant cost.

To obtain higher yields of isobutane, other isomerization processes have been developed. Liquid superacids containing a strong protic acid and a strong Lewis acid have been disclosed (U.S. Pat. Nos. 3,708,553; 3,766,286; 3,839,489; 3,855,346). Because of instability, these catalysts give less than stoichiometric yields of isobutane.

Solid, very strongly acidic materials suitable for catalyzing hydrocarbon reactions, for example the isomerization of n-butane, have been prepared in the prior art by treatment of zirconium oxides with sulfate ion, for example 1N sulfuric acid, and calcining the product at 500° C. for three hours, as disclosed in (1) Hino et al "Reactions of Butane and Isobutane Catalyzed by Zirconium Oxide Treated With Sulfate Ion", *Journal of the American Chemical Society*, Oct. 10, 1979, pages 3469–41. Solid superacids suitable for catalyzing skeletal isomerizations of butane and isobutane have been prepared by exposing $H_4TiO_4$ to 1N sulfuric acid and calcining in air at 500° C., as disclosed in (2) Hino et al, "Reactions of Butane and Isobutane Catalysed by Titanium Oxide Treated with Sulphate Ion", *J.S.C. Chem. Comm.*, 1979, pages 1148–9. (3) Hino et al, "Synthesis of Solid Superacid Catalyst with Acid Strength of $H_0 < -16.04$" disclose a preparation similar to that in reference (1) above, wherein $Zr(OH)_4$ obtained from different sources was calcined at temperatures up to 650° C., and found suitable for reactions of butane in a recirculation reactor at 25° C.

In (4) Ito et al Japanese Patent No. 61.242.641, solid acid catalysts for butane alkylation are prepared by impregnating sulfate-containing materials and rare earth metals or their compounds or supports consisting of Group IV metal hydroxides or oxides, followed by calcination and stabilization. Powdered $Zr(OH)_4$ supports were impregnated with lanthanum nitrate, dried, calcined at 300° C., treated with sulfuric acid, dried and calcined at 550° C. for 3 hours.

In (5) Japanese patent publication 87-344276/49, a solid superacid catalyst was prepared by impregnating a carrier comprising the hydroxide or oxide of a Group III or Group IV metal with a Group VIII metal (the abstract refers to Group VII, but the examples given are of Group VIII metals), for use in producing lower paraffin hydrocarbons from shale oil.

In (6) *Chemical Week*, Nov. 25, 1987, the treatment of zirconium, titanium and iron oxides with sulfuric acids to produce "sulfated" inorganic oxides that show superior catalytic activity for alkylation of ortho-xylene by styrene, is disclosed.

In (7) Baba et al Japanese Patent No. 61-2633932, Nov. 21, 1986, filed May 17, 1985, hydrocarbons are isomerized at reaction temperature below 400° C. using a catalyst obtained by impregnating Group VIII metals, e.g. nickel, platinum, ruthenium, rhodium, palladium, osmium or iridium, and sulfate ion or precursor thereof in a carrier made of Group VI metals, e.g. titanium, zirconium, hafnium, silicon, germanium or tin, and/or hydroxide or oxide of Group III metals, e.g. aluminum, gallium, indium and thallium, and stabilizing by roasting at 450°–800° C. for 5 to 16 hours.

In (8) Veda et al Japanese Patent No. 62-246993, filed Apr. 2, 1986, paraffin hydrocarbons are thermally cracked at 150°–350° C. and over 50 atmospheres hydrogen pressure in the presence of a solid, ulta strongly acidic catalyst made by treating hydroxides or impregnating a Group VIII metal, e.g. nickel, platinum, ruthenium, rhodium, palladium, osmium or iridium, on a supporting body of a hydroxide or oxide of Group III or Group IV metals, e.g. titanium, zirconium, silicon, germanium, tin, aluminum, gallium or indium, followed by treating with sulfuric acid and roasting to stabilize the catalyst.

References (7) and (8) indicate that addition of Group VIII metal improves the catalytic activities of the solid superacids and that these solid superacids are suitable for isomerization of alkanes and xylenes, and cracking of shale oil or coal to light paraffins.

A solid superacid catalyst reported by (9) K. Arata et al, *J. Amer. Chem. Soc.*, 101, 6439 (1979), a sulfuric acid treated zirconium oxide, isomerized n-butane at 100° to 250° C., but the n-butane isomerization below 100° C. is negligible.

The present invention provides a sulfated, very strongly acidic catalyst which contains, in addition to oxide or hydroxide of Group III or Group IV element and Group VIII metal, as in reference (7) above, oxide or hydroxide of a Group V or Group VI or Group VII metal. A superior catalyst is thus obtained for use for example in the isomerization of paraffin hydrocarbons.

The catalysts according to the invention comprise a sulfated and calcined solid mixture of (1) oxide or hydroxide of metal from a first class consisting of Group III and Group IV metals, (2) oxide or hydroxide from a second class consisting of Group V, Group VI or Group VII metal and (3) oxide or hydroxide of Group VIII metal. The weight ratio of metal from the second class to Group VIII metal is in the range from 0.1:1 to 2.0:1, preferably 0.2:1 to 1.0:1. The catalyst preferably contains a major amount of oxide or hydroxide of metal from the first class and a minor amount, preferably in the range from 0.02 to 15.0 weight percent, more preferably 0.1 to 4.5 weight percent, of total metal from the second class and Group VIII metal.

The carrier or support for the catalyst according to the invention is an oxide or hydroxide of a Group III or Group IV element. Examples of suitable such elements are aluminum, gallium, indium, thallium, titanium, zirconium, hafnium, silicon, germanium, tin and lead. Preferred are silicon, aluminum, zirconium and mixtures of two or more thereof.

Metals from Groups V, VI or VII which can be used according to the invention include arsenic, antimony, bismuth, vanadium, niobium, tantalum, selenium, tellurium, chromium, molybdenum, tungsten, manganese and rhenium and mixtures of two or more thereof.

Metals from Group VIII which can be used according to the invention include iron, cobalt, nickel, ruthenium, rhodium, palladium, osmium, iridium and platinum and mixtures of two or more thereof.

The catalysts according to the invention may be prepared for example by impregnating a support of a Group III or Group IV metal oxide or hydroxide with an aqueous solution containing compounds of Group VII and Group VIII metals. Alternatively the support can be impregnated separately with a solution of a Group VII metal compound and a solution of a Group VIII metal compound.

The catalysts according to the invention may also be prepared by co-precipitation of solid hydroxide of (1) Group III or Group IV metals, (2) Group V, Group VI or Group VII metals and (3) Group VIII metals, from aqueous solutions containing compounds of such metals. In such method, the amount of the Group VIII metal hydroxide is typically in the range from 0.01 to 10.0 percent by weight of the total precipitated hydroxide. Mixtures of Group III and Group IV metal oxides or hydroxides, or of two or more from among Group V, Group VI and Group VII metal oxides or hydroxides, may be employed.

Solutions of metal compounds which can be used in the preparation of catalysts according to the invention, by impregnation or co-precipitation, are known in the art. For example, aqueous solution of chloroplatinic acid or tetra-ammine-platinum complex can be used to incorporate platinum in the catalyst. Nitrates of iron and of manganese can be used for example to incorporate those metals in the catalyst. Solutions of zirconium oxychloride or of zirconyl nitrate can be used for example to prepare a zirconium support for the catalyst according to the invention. Various other solutions can be employed as needed.

Sulfate ion may be supplied to the catalyst according to the invention by treatment of the solid catalyst with sulfuric acid, for example 0.01–10N sulfuric acid, preferably 0.1–5N sulfuric acid. Other compounds such as ammonium sulfate capable of providing sulfate ion can be employed. Compounds such as hydrogen sulfide or sulfur dioxide or mercaptans, capable of forming sulfate ions upon calcining, can also be employed. Preferred catalysts for use according to the invention are those which have been sulfated with ammonium sulfate.

The catalysts according to the invention contain substantial amounts of sulfate ion, preferably in amount of 0.5 to 20 weight percent based on total catalyst, and more preferably 5 to 15 weight percent.

The catalysts according to the invention are calcined at a temperature which is preferably in the range from 450°–800° C., more preferably 550°–700° C., and for a period of time in the range from 2 to 30 hours. Combinations of temperature and time can be chosen in order to provide a desired degree of conversion. For example, calcining at 550° C. for 12 hours provides about the same initial conversion of n-butane to isobutane as calcining at 575° C. for 4 hours.

The catalysts according to the invention are in one embodiment of the invention used to isomerize normal alkanes having four to seven carbon atoms, namely butane, pentane, hexane and heptane, to convert the straight chain hydrocarbons into branched chain hydrocarbons having higher octane number for use as motor fuel or, as in the case of butane, having enhanced value as an intermediate for such products as tertiarybutyl alcohol and high octane alkylates.

The isomerization is carried out by contacting the hydrocarbon feed with the solid catalyst at temperatures in the range from 0° C. to 400° C., preferably in the range from 20° to 150° C. and at pressure in the range from 1 to 50 atmospheres. An advantage of the catalysts according to the invention is that they are capable of providing higher yields of desired product at a given temperature than the prior art catalysts, and it is therefore possible to obtain a given yield with the catalyst according to the invention at a lower temperature than that required with the prior art catalysts, and therefore with lesser heat requirements and expense. The catalysts according to the invention also exhibit a beneficial degree of sulfur tolerance. The isomerization may be conducted either in the presence or absence of hydrogen. If conducted in the presence of hydrogen, the mole ratio of hydrogen to hydrocarbon is preferably in the range from 0.1:1 to 10:1. Inert gas such as nitrogen, helium, or argon may be employed. Generally, a temperature is used which is sufficiently high to obtain a desired rate of reaction, but not so high as to result in unnecessarily great heat requirements.

EXAMPLE 1

A sulfated zirconia based catalyst containing the Group VIII metal, iron, and the Group VII metal, manganese, is prepared by the following co-precipitation method:

Suitable amounts of zirconyl nitrate and ferric nitrate and manganese nitrate are dissolved in de-ionized water to make 1.0 liter of solution (A) of concentrations as hereinafter indicated. 130 grams of concentrated ammonium hydroxide are diluted with sufficient de-ionized water to make 1.0 liter of solution (B). 500 milliliters of de-ionized water are added to a 5 liter Morton flask. Solution (A) and solution (B) are added concurrently from two addition funnels to the Morton flask slowly with rapid stirring. The pH of the resulting reaction mixture is kept at about 7.0. The reaction slurry is filtered and the filter cake is washed with de-ionized water several times until the filtrate is nitrate free. The damp cake is applied to perforated plates, placed in a tray and dried overnight at 150° C. The pellets are removed from the tray, transferred to a porcelain dish and calcined in an oven at 500° C. for 4.0 hours. The calcined pellets are added slowly to a beaker containing 1.0 normal sulfuric acid solution at room temperature. The amount of sulfuric acid is determined by the following ratio of 15 milliliters of 1.0 normal sulfuric acid per gram of pellet. The sulfuric acid solution is decanted after the pellets are soaked for 2.0 hours. The pellets are calcined again at 500° C. for 4 hours.

EXAMPLES 2 to 9

The catalysts prepared in Example 1 are used in isomerization of n-butane as follows: In a fixed bed reactor containing 5.0 milliliters of solid catalyst, n-butane (2.2 milliliters of liquid per hour) and nitrogen (30 milliliters per minute) are continuously added from the top of the reactor. The reaction temperature is controlled by an oil circulating heating jacket. The reaction pressure is controlled using a back pressure regulator. The reaction sample is taken from the bottom of the reactor (after the back pressure regulator) by withdrawing the gas mixture using a gas tight syringe. The degree of isomerization is determined on samples taken after two-hour reaction time, using a gas chromatograph equipped with a SE-30 capillary column. The results are shown in the following table:

TABLE 1

Isomerization of n-butane to isobutane (catalyst charge: 5.0 milliliters; n-butane feed; 2.2 milliliters of liquid per hour; nitrogen charge: 30 milliliters per minute).

| Example | Run No. | Catalyst | Isomerization Temperature °C. | Product Composition (% wt) | |
|---|---|---|---|---|---|
| | | | | Isobutane | n-butane |
| 2 | 1 | Neat $ZrO_2$ | 50 | 0.09 | 99.90 |
| | 2 | " | 75 | 0.11 | 99.89 |
| | 3 | " | 100 | 0.29 | 99.70 |
| 3 | 4 | 1.5% Ru on $ZrO_2$ | 50 | 0.62 | 99.27 |
| | 5 | " | 75 | 3.40 | 95.98 |
| | 6 | " | 100 | 4.55 | 94.94 |
| 4 | 7 | 1.5% Fe on $ZrO_2$ | 50 | 2.11 | 97.89 |
| | 8 | " | 75 | 11.86 | 88.14 |
| | 9 | " | 100 | 23.29 | 75.70 |
| 5 | 10 | 2.0% Fe on $ZrO_2$ | 50 | 2.26 | 97.74 |
| | 11 | " | 75 | 10.09 | 89.91 |
| | 12 | " | 100 | 18.36 | 81.12 |
| 6 | 13 | 1.5% Fe, 0.5% Mn on $ZrO_2$ | 23 | 2.37 | 97.62 |
| | 14 | " | 50 | 6.50 | 93.50 |
| | 15 | " | 100 | 24.58 | 74.39 |
| 7 | 16 | 1.0% Fe, 1.0% Mn on $ZrO_2$ | 23 | 4.07 | 95.93 |
| | 17 | " | 50 | 9.31 | 90.40 |
| | 18 | " | 75 | 11.20 | 88.51 |
| 8 | 19 | 0.5% Fe, 1.5% Mn on $ZrO_2$ | 23 | 1.47 | 98.53 |
| | 20 | " | 50 | 1.31 | 98.69 |
| | 21 | " | 75 | 0.88 | 99.12 |
| 9 | 22 | 3.75% Fe, 1.25% Mn on $ZrO_2$ | 23 | 4.58 | 95.42 |
| | 23 | " | 50 | 10.29 | 89.71 |
| | 24 | " | 75 | 15.0 | 85.0 |
| | 25 | " | 100 | 5.04 | 94.96 |

The catalyst used in Example 2 above was zirconium without added Group VIII metal. The catalyst used in Example 3 was zirconium with 1.5% added ruthenium, prepared as described in Example 1, but employing the Group VIII metal, ruthenium, in place of iron. The catalysts used in Examples 4 to 9 were zirconium with the indicated added amounts of iron, or of iron and manganese, prepared as described in Example 1. All of the catalysts in Examples 2 to 9 were sulfated and calcined as described in Example 1.

The following table presents data from the above Table 1 to show the effect of varying catalyst composition on the isomerization results at a given temperature:

| Run No. | Catalyst | Isomeriz. Temp. °C. | Isobutane % in Isomeriz. Prod. |
|---|---|---|---|
| 11 | 2.0% Fe on $ZrO_2$ | 75 | 10.09 |
| 12 | 2.0% Fe on $ZrO_2$ | 100 | 18.36 |
| 15 | 1.5% Fe, 0.5% Mn on $ZrO_2$ | 100 | 24.58 |
| 18 | 1.0% Fe, 1.0% Mn on $ZrO_2$ | 75 | 11.20 |
| 21 | 0.5% Fe, 1.5% Mn on $ZrO_2$ | 75 | 0.88 |
| 24 | 3.75% Fe, 1.25% Mn on $ZrO_2$ | 75 | 15.00 |
| 25 | 3.75% Fe, 1.25% Mn on $ZrO_2$ | 100 | 5.04 |

Comparison of Runs 12 and 15 shows the increase in isomerization activity by using Group VIII and Group VII metals together, in place of the same total amount of Group VIII metal. Runs 18 and 21 show the effect of varying the ratio of Group VIII metal to Group VII metal in the catalyst, and shows that unsatisfactory results are obtained when the ratio is 1:3. The ratio of Group VIII metal to Group VII metal may be about 1 to 1 (as in Run 18) or somewhat lower with satisfactory results, but a ratio higher than 1 to 1 is preferred. Comparisons of Runs 15 and 25 show that, at a ratio of Group VIII metal to Group VII metal of 3 to 1, better results are obtained with total amount of Group VIII and Group VII metal of 2.0 than with total amount of Group VIII and Group VII metal of 5.0.

EXAMPLES 10-16

Sulfated zirconia based catalysts containing iron and manganese are prepared by a co-precipitation method similar to that of Example 1, except that ammonium sulfate, rather than sulfuric acid, is used to sulfate the catalyst, and the sulfation is done prior to any calcining of the catalyst. The dried pellets from the overnight drying step are treated with ammonium sulfate to incorporate 4% or 8% of sulfate ion in the catalyst, using incipient wetness technique, then calcined.

The catalysts in Examples 10 through 14 were precipitated at pH 7.0. The catalyst in Example 15 was precipitated at pH 4.0; the catalyst in Example 16 at pH 9.5. The catalysts in Examples 10, 11, 13, 15 and 16 contained 4% sulfate ion; the catalysts in Examples 12 and 14, 8% sulfate ion. The catalysts in Examples 10, 11, 14, 15 and 16 were calcined 16 hours at 600° C.; the catalyst in Example 12 was calcined 20 hours at 625° C.; the catalyst in Example 13 was calcined 24 hours at 600° C.

The catalysts are used in isomerization of n-butane by the procedure described in Examples 2-9, with results as follows:

TABLE 2

| EXAMPLE | RUN NO. | CATALYST | ISOMERIZATION TEMPERATURE °C. | PRODUCT COMPOSITION (% WT) | |
|---|---|---|---|---|---|
| | | | | ISOBUTANE | n-BUTANE |
| 10 | 26 | NEAT ZrO$_2$ | 25 | 0.61 | 99.23 |
| | 27 | " | 50 | 3.98 | 95.77 |
| | 28 | " | 75 | 10.74 | 88.70 |
| 11 | 29 | 1.5% Fe, 0.5% Mn on ZrO$_2$ | 25 | 1.67 | 98.25 |
| | 30 | " | 50 | 34.11 | 64.54 |
| | 31 | " | 75 | 44.29 | 53.02 |
| 12 | 32 | 1.5% Fe, 0.5% Mn on ZrO$_2$ | 25 | 3.26 | 96.50 |
| | 33 | " | 50 | 35.75 | 62.78 |
| | 34 | " | 75 | 51.34 | 43.55 |
| 13 | 35 | 1.5% Fe, 0.5% Mn on ZrO$_2$ | 25 | 3.14 | 96.59 |
| | 36 | " | 50 | 28.27 | 70.71 |
| | 37 | " | 75 | 55.08 | 40.25 |
| 14 | 38 | 1.5% Fe, 0.5% Mn on ZrO$_2$ | 25 | 0.76 | 99.24 |
| | 39 | " | 50 | 13.42 | 86.35 |
| | 40 | " | 75 | 40.69 | 57.55 |
| 15 | 41 | 1.5% Fe, 0.5% Mn on ZrO$_2$ | 25 | 1.02 | 98.95 |
| | 42 | " | 50 | 17.89 | 81.32 |
| | 43 | " | 75 | 37.96 | 59.62 |
| 16 | 44 | 1.5% Fe, 0.5% Mn on ZrO$_2$ | 25 | 1.70 | 98.30 |
| | 45 | " | 50 | 26.05 | 73.12 |
| | 46 | " | 75 | 45.57 | 51.64 |

Other suitable embodiments of the invention are obtained when other elements, or mixtures thereof, from Group III or Group IV are used in place of zirconium, when other metals or mixtures thereof from Group V, Group VI or Group VII are used in place of manganese, and when other Group VIII metals are used in place of iron.

The invention claimed is:

1. A catalyst comprising a sulfated and calcined solid mixture of (1) oxide or hydroxide of element from a first class consisting of Group III or Group IV elements, (2) oxide or hydroxide of metal from a second class consisting of Group V, Group VI or Group VII metals, and (3) oxide or hydroxide of Group VIII metal, the ratio of metal from said second class to Group VIII metal being in the range from 0.1:1 to 2.0:1.

2. Composition according to claim 1 wherein the catalyst contains, from said first class, silicon, aluminum, zirconium, or mixtures comprising two or more thereof.

3. Composition according to claim 2 wherein said element from said first class is zirconium.

4. Composition according to claim 1 wherein said Group VIII metal is iron, cobalt, nickel, ruthenium, rhodium, palladium, osmium, iridium or platinum or mixtures comprising two or more thereof.

5. Composition according to claim 4 wherein said metal is iron.

6. Composition according to claim 1 wherein said metal from said second class is manganese, rhenium, chromium, molybdenum, tungsten, vanadium, niobium, arsenic, antimony or bismuth or mixtures comprising two or more thereof.

7. Composition according to claim 6 wherein said metal is manganese.

8. Composition according to claim 1 wherein said catalyst has been sulfated with ammonium sulfate.

9. Composition according to claim 1 wherein said catalyst contains 5 to 15 weight percent of sulfate ion.

10. Composition according to claim 4 wherein said metal is cobalt.

11. Composition according to claim 6 wherein said metal is molybdenum.

12. Catalyst according to claim 1 containing no substantial amount of ruthenium.

13. Catalyst according to claim 1 containing no substantial amount of platinum.

* * * * *